US009186526B2

(12) United States Patent
Akagane

(10) Patent No.: US 9,186,526 B2
(45) Date of Patent: Nov. 17, 2015

(54) ULTRASONIC TREATMENT PROBE

(71) Applicant: OLYMPUS CORPORATION, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/132,316

(22) Filed: Dec. 18, 2013

(65) Prior Publication Data
US 2014/0188012 A1 Jul. 3, 2014

Related U.S. Application Data

(63) Continuation of application No. PCT/JP2013/064609, filed on May 27, 2013.

(60) Provisional application No. 61/654,409, filed on Jun. 1, 2012.

(51) Int. Cl.
*A61N 7/00* (2006.01)
*A61B 17/32* (2006.01)

(52) U.S. Cl.
CPC .......... *A61N 7/00* (2013.01); *A61B 17/320068* (2013.01); *A61B 2017/320096* (2013.01)

(58) Field of Classification Search
CPC ........... A61B 17/320068; A61B 2017/320096; A61B 2019/5276; A61B 17/2258; A61B 8/12; A61B 8/4281; A61N 7/00; A61N 2007/0004
See application file for complete search history.

(56) References Cited

U.S. PATENT DOCUMENTS

| 2001/0027325 | A1* | 10/2001 | Beaupre ..................... 606/169 |
| 2005/0021065 | A1 | 1/2005 | Yamada et al. |
| 2007/0225608 | A1 | 9/2007 | Houser et al. |
| 2008/0300611 | A1* | 12/2008 | Houser et al. ................ 606/167 |
| 2009/0069712 | A1* | 3/2009 | Mulvihill et al. ............ 600/564 |
| 2011/0040213 | A1* | 2/2011 | Dietz et al. ...................... 601/2 |

(Continued)

FOREIGN PATENT DOCUMENTS

| JP | A-01-171537 | 7/1989 |
| JP | U-02-123216 | 10/1990 |
| JP | A-2005-40222 | 2/2005 |
| JP | A-2007-268260 | 10/2007 |

OTHER PUBLICATIONS

Dec. 11, 2014 International Preliminary Report on Patentability issued in International Patent Application No. PCT/JP2013/064609.

(Continued)

*Primary Examiner* — Amanda Lauritzen Moher
(74) *Attorney, Agent, or Firm* — Oliff PLC

(57) ABSTRACT

An ultrasonic probe includes a first coupled vibration member and a second coupled vibration member each of which extends along a longitudinal axis between a first anti-node position of an ultrasonic vibration and a second anti-node position of the ultrasonic vibration located to a distal direction side of the first anti-node position. The second coupled vibration member vibrates in the same mode as the first coupled vibration member. A first groove of the first coupled vibration member and a second groove of the second coupled vibration member cooperate with each other and thereby form at least a part of a passage inside a multiple-members vibrating portion formed by the first coupled vibration member and the second coupled vibration member.

6 Claims, 9 Drawing Sheets

(56) References Cited

U.S. PATENT DOCUMENTS

| | | | |
|---|---|---|---|
| 2012/0078278 A1* | 3/2012 | Bales et al. | 606/169 |
| 2013/0131705 A1* | 5/2013 | Akagane | 606/169 |
| 2014/0066818 A1* | 3/2014 | Akagane | 601/2 |

OTHER PUBLICATIONS

Jul. 2, 2013 International Search Report issued in International Application No. PCT/JP2013/064609 (with translation).

* cited by examiner

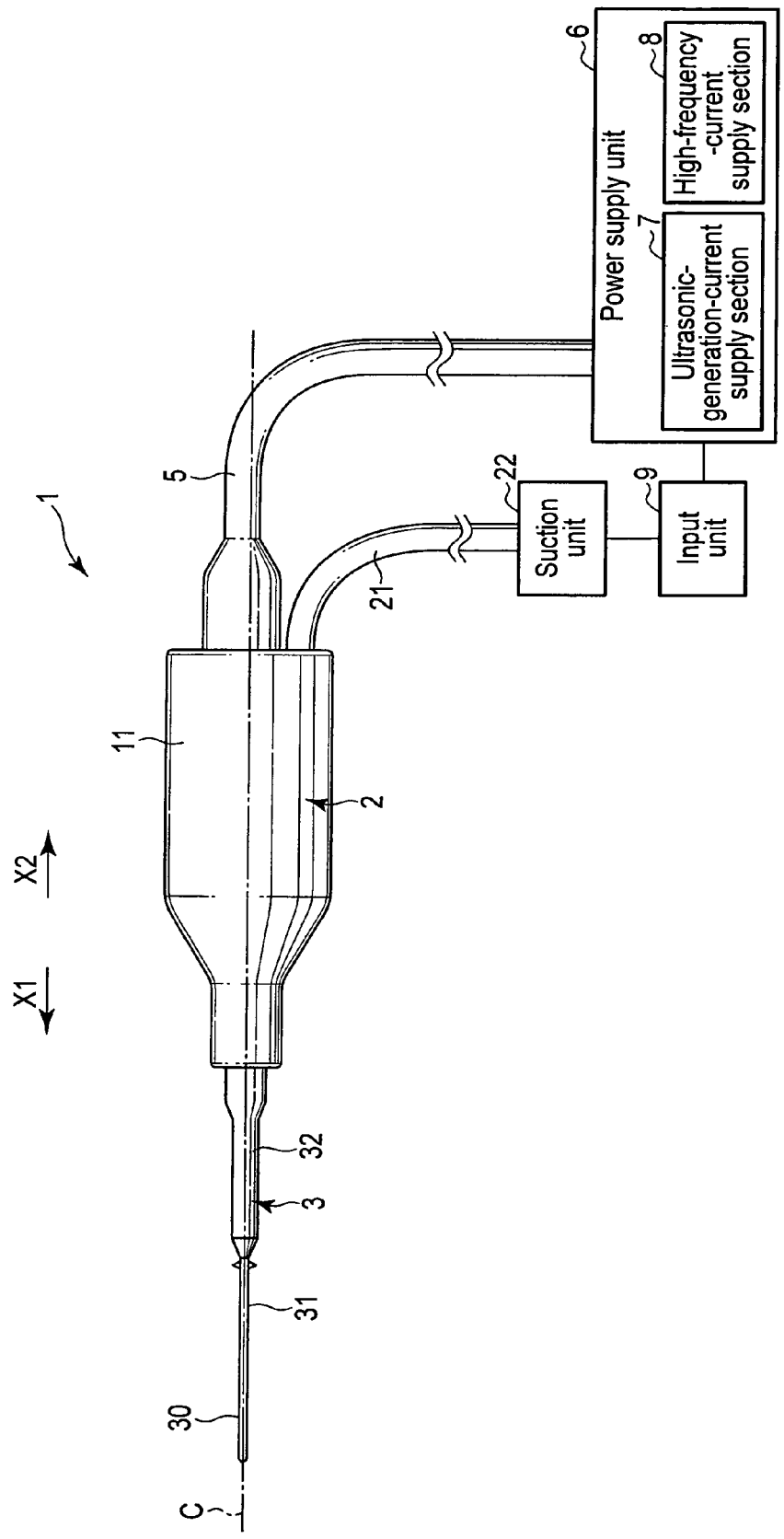
F I G. 1

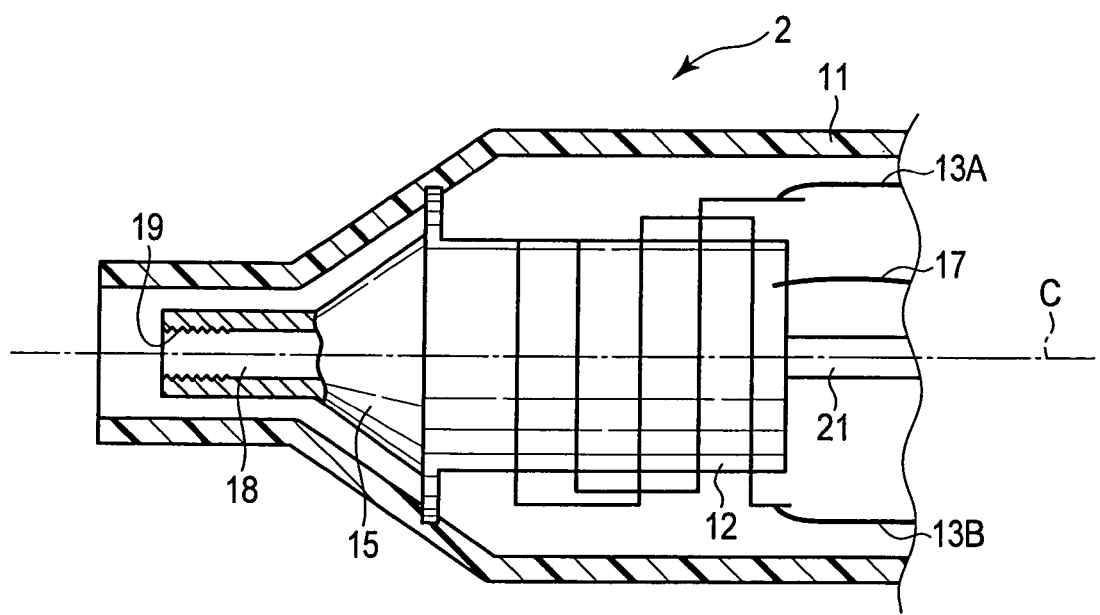
F I G. 2

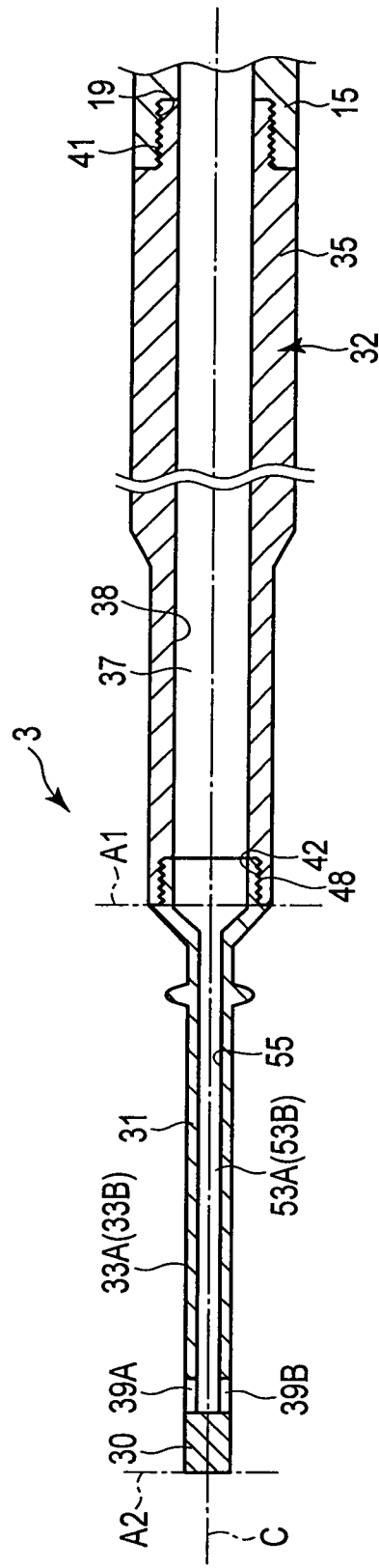
F I G. 3

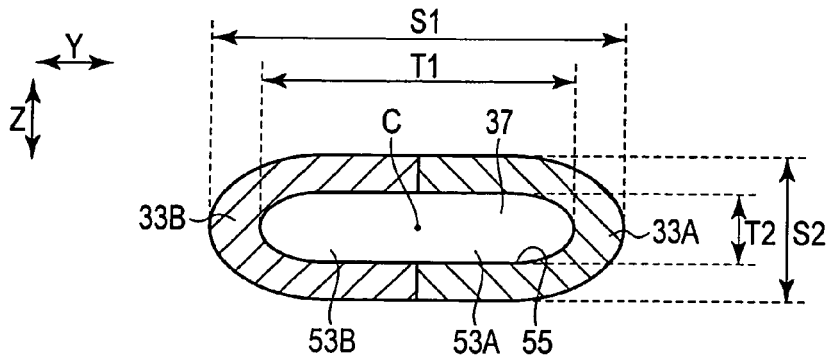
F I G. 6
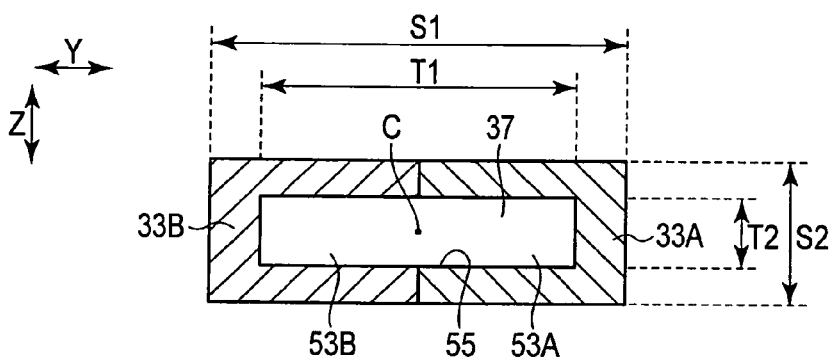
F I G. 7
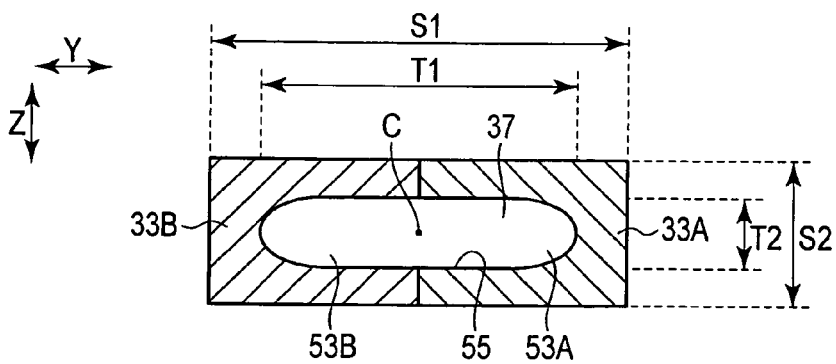
F I G. 8

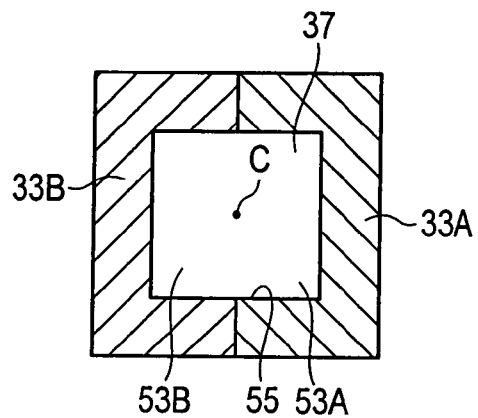
F I G. 11
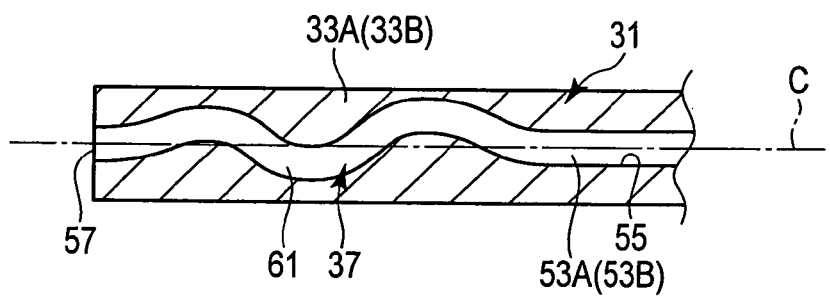
F I G. 12
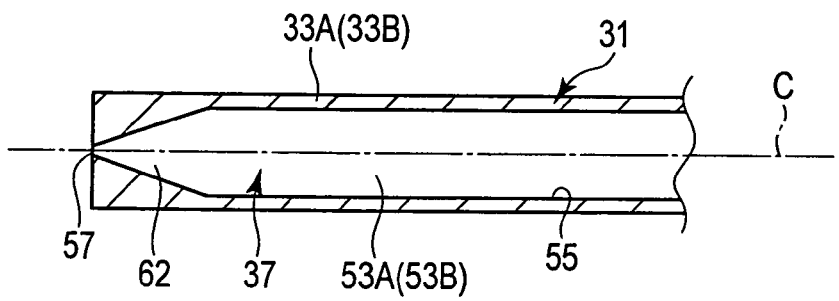
F I G. 13

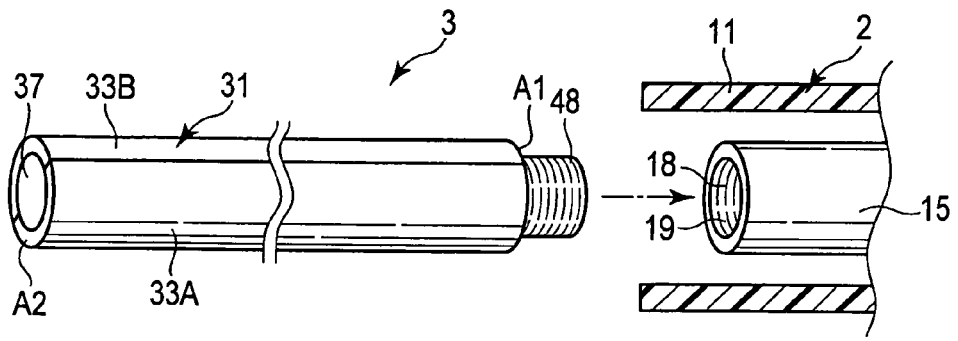
F I G. 14
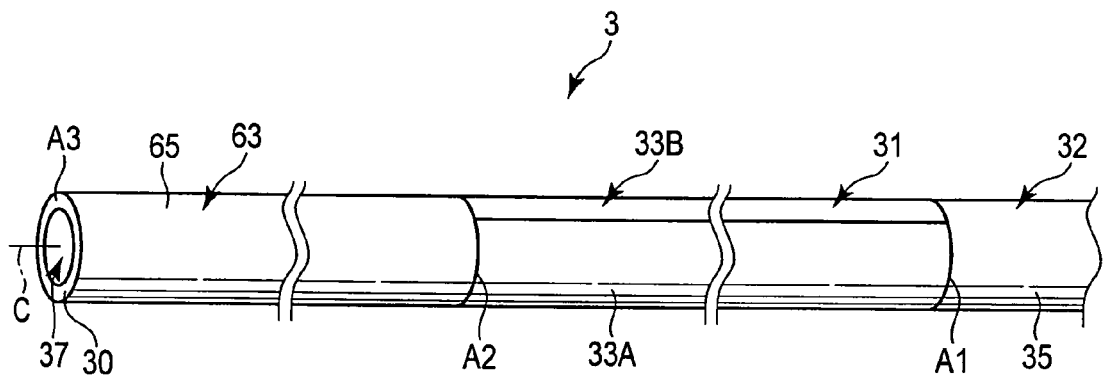
F I G. 15
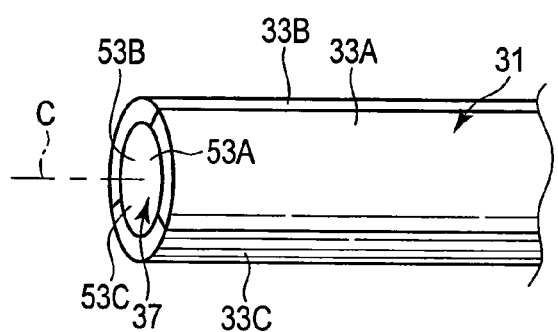
F I G. 16

ULTRASONIC TREATMENT PROBE

CROSS-REFERENCE TO RELATED APPLICATIONS

This is a Continuation Application of PCT Application No. PCT/JP2013/064609, filed May 27, 2013 and based upon and claiming the benefit of priority from prior U.S. Provisional Application No. 61/654,409, filed Jun. 1, 2012, the entire contents of which are incorporated herein by reference.

BACKGROUND OF THE INVENTION

1. Field of the Invention

The present invention relates to an ultrasonic probe which can transmit an ultrasonic vibration along a longitudinal axis from a proximal direction toward a distal direction.

2. Description of the Related Art

The specification of U.S. Patent Application Publication No. 2005/0021065 discloses an ultrasonic probe extending along a longitudinal axis. The ultrasonic probe is configured to transmit an ultrasonic vibration, which is caused by an ultrasonic vibrator (ultrasonic transducer) as an ultrasonic generator, from a proximal direction toward a distal direction along a longitudinal axis. A distal treatment section which is configured to treat a treatment object such as living tissue is provided to (at) a distal end portion of the ultrasonic probe. As the ultrasonic vibration is transmitted to the distal treatment section, the treatment object is resected by the distal treatment section. Further, a suction passage is formed inside the ultrasonic probe with extending along the longitudinal axis from the distal end portion toward the proximal direction. The resected treatment object is suctioned through the suction passage.

BRIEF SUMMARY OF THE INVENTION

According to one aspect of the invention, an ultrasonic treatment probe which is configured to transmit an ultrasonic vibration from a proximal direction toward a distal direction along a longitudinal axis, a multiple-members vibrating portion that includes a plurality of coupled vibration members, each of the coupled vibration members extending in a lengthwise direction along the longitudinal axis, and each of the coupled vibration members having an inner surface, wherein a groove is formed in the lengthwise direction along the longitudinal axis by the inner surface in each of the coupled vibration members, the coupled vibration members being coupled to each other when the inner surface of each of the coupled vibration members face each other, such that a passage extending from the proximal direction toward the distal direction is formed inside the multiple-members vibrating portion, and the multiple-members vibrating portion is configured to transmit the ultrasonic vibration such that each of the coupled vibration members vibrates in a same vibration mode, and such that a first anti-node position is located at a proximal end of the multiple-members vibrating portion, and a second anti-node position is located at a distal end of the multiple members vibrating portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing an ultrasonic treatment device according to a first embodiment of the invention;

FIG. 2 is a cross-sectional view schematically showing a configuration of a vibration generation unit according to the first embodiment;

FIG. 3 is a cross-sectional view schematically showing an ultrasonic probe according to the first embodiment;

FIG. 6 is a cross-sectional view cut along line VI-VI in FIG. 4.

FIG. 7 is a cross-sectional view schematically showing a cross-section of a multiple-members vibrating portion of the ultrasonic probe, which is perpendicular to the longitudinal axis, according to a first modification;

FIG. 8 is a cross-sectional view schematically showing a cross-section of the multiple-members vibrating portion of the ultrasonic probe, which is perpendicular to the longitudinal axis, according to a second modification;

FIG. 11 is a cross-sectional view schematically showing a cross-section of the multiple-members vibrating portion of the ultrasonic probe, which is perpendicular to longitudinal axis, according to a third modification;

FIG. 12 is a cross-sectional view schematically showing a cross-section of the multiple-members vibrating portion of the ultrasonic probe, which is parallel to the longitudinal axis, according to a fourth modification;

FIG. 13 is a cross-sectional view schematically showing a cross-section of a multiple-members vibrating portion of the ultrasonic probe, which is parallel to the longitudinal axis, according to a fifth modification;

FIG. 14 is a schematic view for explaining connection between the ultrasonic probe and the ultrasonic generation unit, according to a sixth modification;

FIG. 15 is a perspective view schematically showing the ultrasonic probe according to a seventh modification; and FIG. 16 is a perspective view schematically showing a configuration of a multiple-members vibrating portion of the ultrasonic probe, according to an eighth modification.

DETAILED DESCRIPTION OF THE INVENTION

First Embodiment

Figure 4:
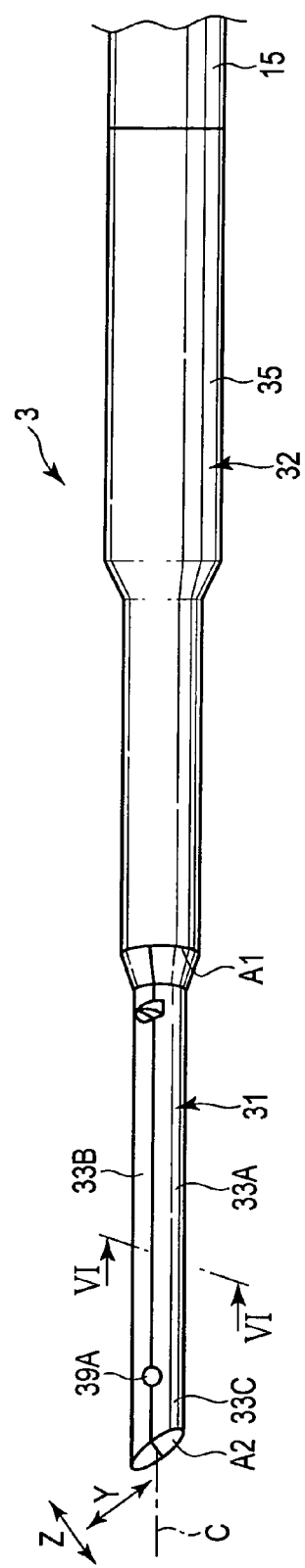
FIG. 4 is a perspective view schematically showing the ultrasonic probe according to the first embodiment.

The first embodiment of the invention will be described with reference to FIGS. 1 to 6. FIG. 1 is a schematic view showing an ultrasonic treatment device according to the embodiment. As shown in FIG. 1, the ultrasonic treatment device 1 has a longitudinal axis C. Here, one of two directions parallel to the longitudinal axis C is supposed to be a distal direction (the direction of arrow X1 in FIG. 1), and the other one opposite to the distal direction is supposed to be a proximal direction (the direction of arrow X2 in FIG. 1). An ultrasonic treatment apparatus 1 includes a vibration generation unit 2, and a cylindrical ultrasonic probe 3 extending along the longitudinal axis C.

The vibration generation unit 2 include a vibrator case (transducer case) 11. One end of a cable 5 is connected to a proximal end of the vibrator case 11. The other end of the cable 5 is connected to a power supply unit 6. The power supply unit 6 includes an ultrasonic-generation-current supply section 7, and a high-frequency-current supply section 8. An input unit 9 is connected to the power supply unit 6.

FIG. 2 shows a configuration of the vibration generation unit 2. As shown in FIG. 2, an ultrasonic vibrator (ultrasonic transducer) 12 as a vibration generator including piezoelectric elements which are configured to convert an electric current into an ultrasonic vibration is formed inside the vibrator case (oscillator case) 11. An end of each of electric wirings 13A and 13B is connected to the ultrasonic vibrator (ultrasonic oscillator) 12. Each of the electric wirings 13A and 13B extends inside the cable 5, and has other end connected to the ultrasonic-generation-current supply section 7 of the power supply unit 6. The ultrasonic vibration occurs in the ultrasonic vibrator 12 as an electric current is supplied to the ultrasonic vibrator 12 through the electric wirings 13A and 13B from the ultrasonic-generation-current supply section 7. A horn 15 which is configured to amplify the amplitude of the ultrasonic vibration is coupled (connected) to the distal direction side of the ultrasonic transducer 12. The horn 15 is attached to the vibrator case 11.

One end of an electric wiring 17 is connected to the ultrasonic vibrator 12. The electric wiring 17 extends inside the cable 5, and has the other end connected to the high-frequency-current supply section 8 of the power supply unit 6. A high frequency current is transmitted to the ultrasonic vibrator 12 and the horn 15 through the electric wiring 17 from the high-frequency-current supply section 8.

A space 18 is formed in the ultrasonic oscillator 12 and the horn 15, with the longitudinal axis C being an axial center. Further, a female screw portion 19 is formed at a distal end portion of an inner peripheral surface of the horn 15. One end of a tube member 21 is connected to the space 18. As shown in FIG. 1, the tube component 21 is extended outside of the vibrator case 11, and the other end tube member 21 is connected to the suction unit 22. A suction unit 22 is electrically connected to the input unit 9.

Figure 5:
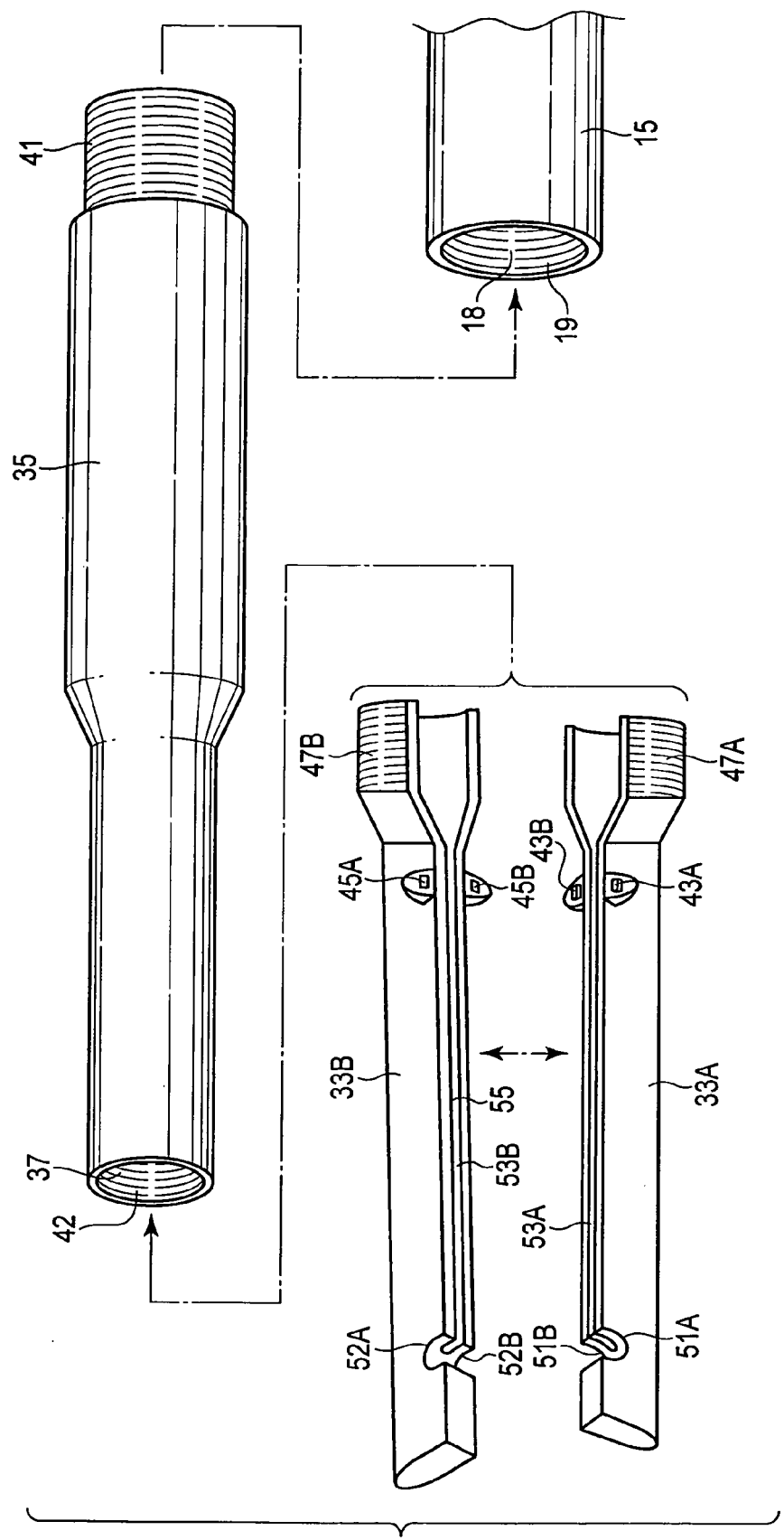
FIG. 5 is a perspective view schematically showing the ultrasonic probe exploded into individual members, according to the first embodiment.

FIGS. 3 to 5 show a configuration of the ultrasonic probe 3. As shown in FIGS. 3 to 5, in a distal end portion of the ultrasonic probe 3, there is provided a distal treatment section 30 such as an electric knife configured to treat a treatment object (treatment target) such as living tissue. Further, the ultrasonic probe 3 includes a multiple-members vibrating portion 31, and a single-member vibrating portion 32 provided to the proximal direction side of the multiple-members vibrating portion 31. The distal treatment section 30 is positioned to a distal end portion of the multiple-members vibrating portion 31. The multiple-members vibrating portion 31 includes a plurality of coupled vibration members 33 made of titanium. In the present embodiment, the multiple-members vibrating portion 31 is constituted by two members, and includes a coupled vibration member 33A as a first member, and a coupled vibration member 33B as a second member.

Further, the single-member vibrating portion 32 is formed by an integral vibration member 35 alone, which is made of titanium.

A passage 37 is defined inside the ultrasonic probe 3 by a passage defining portion 38. The passage 37 is extended toward the proximal direction from the distal end portion (distal treatment section 30) of the ultrasonic probe 3. In the present embodiment, the passage 37 extends along the longitudinal axis C up to the proximal end of the ultrasonic probe 3. Two openings 39A and 39B, which open with respect to the outside, are provided on an outer peripheral portion of the distal end portion (distal treatment section 30) of the ultrasonic probe 3. The openings 39A and 39B are positioned apart from each other in directions around the longitudinal axis. Each of the openings 39A and 39B communicates with the passage 37.

A male screw portion 41 is provided on an outer peripheral portion of the proximal end portion of the ultrasonic probe 3, integrally with the integral vibration member 35. As the male screw portion 41 is screwed in the female screw portion 19 of the horn 15, the integral vibration member 35 of the ultrasonic probe 3 is attached to the distal direction side of the horn 15. When the integral vibration member 35 is attached to the horn 15, the male screw portion 41 is positioned to the proximal direction side of the single-member vibrating portion 32 and to an inner peripheral direction side of the horn 15. As described above, the male screw portion 41 is a joint portion which connects the vibration generation unit 2 directly to the proximal direction side of the single-member vibrating portion 32.

The integral vibration member 35 is formed in a cylindrical shape, and the passage 37 is partially defined by an inner peripheral portion of the integral vibration member 35. That is, the inner peripheral portion of the integral vibration member 35 is a part of the passage defining portion 38. A female screw portion 42 is formed in the inner peripheral portion of the distal end portion of the integral vibration member 35.

Engagement protrusions 43A and 43B protruding toward the coupled vibration member 33B are formed in a proximal end portion of the coupled vibration member 33A. Further, engagement grooves 45A and 45B are provided to a proximal end portion of the coupled vibration member 33B. The engagement protrusion 43A can be engaged in the engagement groove 45A, and the engagement protrusion 43B can be engaged in the engagement groove 45B. As each of the engagement protrusions 43A and 43B engages with the corresponding engagement groove 45A or 45B, the coupled vibration members 33A and 33B are coupled together, to be positioned with respect to each other, thereby forming the multiple-members vibrating portion 31.

In the ultrasonic probe 3, a male-screw component 47A is formed integrally with the coupled vibration member 33A, and a male screw component 47B is formed integrally with the coupled vibration member 33B. When the coupled vibration members 33A and 33B are connected to each other, a male screw portion 48 is formed by the male screw components 47A and 47B. As the male screw portion 48 is screwed in a female screw portion 42 of the integral vibration member 35, the coupled vibration members 33A and 33B are attached to the distal direction side of the integral vibration member 35. When the coupled vibration members 33A and 33B are attached to the integral vibration member 35, the male screw portion 48 is positioned to the proximal direction side of the multiple-members vibrating portion 31, and is also positioned to the inner peripheral direction side of the integral vibration member 35. As described above, the male screw portion 48 is a joint portion which connects the single-member vibrating portion 32 directly to the proximal direction side of the multiple-members vibrating portion 31.

Notches 51A and 51B are provided to the coupled vibration member 33A. Also, notches 52A and 52B are provided to the coupled vibration member 33B. When the coupled vibration members 33A and 33B are coupled to each other, an opening 39A is formed by the notches 51A and 52A. When the coupled vibration members 33A and 33B are connected to each other, an opening 39B is formed by the notches 51B and 52B.

The ultrasonic probe 3 is coupled to the vibration generation unit 2 by attaching the integral vibration member 35 to the horn 15 and by attaching the coupled vibration members 33A and 33B to the integral vibration member 35. When the ultrasonic probe 3 is connected to the vibration generation unit 2, a proximal end of the passage 37 communicates with the space 18 formed inside the horn 15 and the ultrasonic vibrator 12.

When the ultrasonic probe 3 is coupled to the vibration generation unit 2, the ultrasonic probe 3 can transmit the ultrasonic vibration generated by the ultrasonic vibrator 12 along the longitudinal axis C from the proximal direction toward the distal direction. By transmitting the ultrasonic vibration, the ultrasonic probe 3 performs a longitudinal vibration whose transmission direction and vibration directions are parallel to the longitudinal axis C. Further, when the ultrasonic probe 3 is coupled to the vibration generation unit 2, a high frequency current transmitted to the horn 15 is further transmitted up to the distal treatment section 30 along the longitudinal axis C.

When the ultrasonic vibration is transmitted to the ultrasonic probe 3, the proximal end of the multiple-members vibrating portion (joint between the multiple-members vibrating portion 31 and the single-member vibrating portion 32) is a first anti-node position (loop position) A1 of the ultrasonic vibration, and the distal end of the multiple-members vibrating portion 31 is a second anti-node position A2 of the ultrasonic vibration, which is located to the distal direction side of the first anti-node position A1. The multiple-members vibrating portion 31 is formed by coupling the coupled vibration members 33A and 33B with respect to each other. Therefore, in the multiple-members vibrating portion 31, the coupled vibration members 33A and 33B extend along the longitudinal axis C between the first anti-node position (loop position) A1 and the second anti-node position (loop position) A2. The ultrasonic vibration is transmitted to the multiple-members vibrating portion 31 from the single-member vibrating portion 32, at the first anti-node position A1. That is, the proximal end of the multiple-members vibrating portion 31 and the distal end of the single-member vibrating portion 32 are connected to each other at the first anti-node position A1. Further, the second anti-node position A2 corresponds to the distal end of the ultrasonic probe 3.

Each one of the coupled vibration members 33A and 33B vibrates in the same vibration mode as the other one when the ultrasonic vibration is transmitted to the ultrasonic probe 3. Further, the integral vibration member 35 vibrates in the same vibration mode as the coupled vibration members 33A and 33B when the ultrasonic vibration is transmitted to the ultrasonic probe 3. For example, each of the coupled vibration member 33A and 33B and the vibration member 35 is designed to longitudinally vibrate at a frequency of 47 Hz.

The passage defining portion 38 of the ultrasonic probe 3 includes a groove defining portion 55 which defines the groove 53A to the coupled vibration member 33A and which defines the groove 53B to the coupled vibration member 33B. When the coupled vibration members 33A and 33B are connected to each other, a part of the passage 37 is formed by the grooves 51A and 52A. That is, the groove 53A of the coupled vibration member 33A cooperates with the groove 53B of the coupled vibration member 33B so as to form the part of the passage 37 inside the multiple-members vibrating portion 31.

FIG. 6 is a sectional view cut along line VI-VI in FIG. 4. As shown in FIG. 6, in a cross-section perpendicular to the longitudinal axis C, the multiple-members vibrating portion 31 has an elliptic cross-sectional shape. In the cross-section of the multiple-members vibrating portion 31 perpendicular to the longitudinal axis C, a first cross-sectional dimension S1 in first perpendicular directions (directions of arrow Y in FIG. 4 and FIG. 6) perpendicular to the longitudinal axis C is greater than a second cross-sectional dimension S2 in second perpendicular directions (the directions of arrow Z in FIG. 4 and FIG. 6) perpendicular to the longitudinal axis and perpendicular to the first perpendicular directions. In the multiple-members vibrating portion 31, the opening 39A is open toward one of the second perpendicular directions, and the opening 39B is open toward the other one of the second perpendicular directions.

Also, in the cross-section of the multiple-members vibrating portion 31 perpendicular to the longitudinal axis C, a cross-sectional shape of the passage 37 is shaped in an analogous form (analogous shape) with respect to the cross-sectional shape of the multiple-members vibrating portion 31. Further, in the cross-section of the multiple-members vibrating portion 31 perpendicular to the longitudinal axis C, a first passage dimension T1 of the passage 37 in first perpendicular directions is greater than a second passage dimension T2 of the passage 37 in second perpendicular directions. That is, each of the grooves 53A and 53B is defined to the corresponding coupled vibration member 33A or 33B in a manner of forming an elliptic cross-sectional shape of the passage, in which the first passage dimension T1 of the passage 37 in the first perpendicular directions is greater than the second passage dimension T2 of the passage 37 in the second perpendicular directions, in the cross-section of the multiple-members vibrating portion 31 perpendicular to the longitudinal axis C. A first ratio R1 of the first passage dimension T1 of the passage 37 with respect to the first cross-sectional dimension S1 of the multiple-members vibrating portion 31 is equal to a second ratio R2 of the second passage dimension T2 of the passage 37 with respect to the second cross-sectional dimension S2 of the multiple-members vibrating portion 31.

A manufacturing method of the ultrasonic probe 3 will now be described. To manufacture the ultrasonic probe 3, the integral vibration member 35 is formed first. The integral vibration member 35 is formed by drilling a hole in a columnar member through a gun drill process. A part of the passage 37 is formed inside the integral vibration member 35 by the gun drill process. Here, when the integral vibration member 35 is formed, the female screw portion 42 is formed in the integral vibration member 35, and the male screw portion 41 is formed integrally with the integral vibration member 35.

Next, the coupled vibration members 33A and 33B are formed. At this time, the groove 53A is formed in the coupled vibration member 33A by a cutting process, and the groove 53B is formed in the coupled vibration member 33B by a cutting process. When the coupled vibration member 33A is completely formed, the coupled vibration member 33A is provided with the engagement protrusions 43A and 43B and the notches 51A and 51B, and the male screw component 47A is formed integrally with the coupled vibration member 33A. When the coupled vibration member 33B is completely formed, the coupled vibration member 33B is provided with the engagement grooves 45A and 45B and the notches 52A and 52B, and the male screw component 47B is formed integrally with the coupled vibration member 33B.

Each of the engagement protrusions 43A and 43B is engaged in the corresponding engagement groove 45A or 45B, thereby connecting the coupled vibration members 33A and 33B with respect to each other. In this manner, the multiple-members vibrating portion 31 is formed. At this time, each one of the grooves 53A and 53B of the coupled vibration members 33A and 33B cooperate with the groove (53A or 53B) of the other one of the coupled vibration members (33A and 33B), thereby forming a part of the passage 37 inside the multiple-members vibrating portion 31. In the cross-section of the multiple-members vibrating portion 31 perpendicular to the longitudinal axis C, the cross-sectional shape of the passage 37 is formed in an elliptic shape in which the first passage dimension T1 of the passage 37 in the first perpendicular directions is greater than the second passage dimension T2 of the passage 37 in the second perpendicular directions. By connecting the coupled vibration members 33A and 33B with respect to each other, the male screw portion 48 is formed by the male screw components 47A and 47B. Further, by coupling the coupled vibration members 33A and 33B with respect to each other, the opening 39A is formed by the notches 51A and 52A, and the opening 39B is formed by the notches 51B and 52B.

Further, the male screw portion 48 is screwed in the female screw portion 42 of the integral vibration member 35, and the coupled vibration members 33A and 33B are thereby attached to the distal direction side of the integral vibration member 35. In this manner, the ultrasonic probe 3 is manufactured.

Here, a hole whose cross-sectional shape is not perfectly circular but is elliptic in the cross-section perpendicular to the longitudinal axis C cannot be formed in a columnar member by a gun drill process. Therefore, the gun drill process cannot be used when the passage 37 has a part whose cross-sectional shape perpendicular to the longitudinal axis C is not perfectly circular. Inability to use the gun drill process causes deterioration in work efficiency of forming a hole to form a part of the passage 37 in the columnar member.

Hence, in the present embodiment, the groove 53A is formed in the coupled vibration member 33A and the groove 53B is formed in the coupled vibration member 33B, so as to connect the coupled vibration members 33A and 33B with respect to each other. A part of the passage 37 whose cross-section perpendicular to the longitudinal axis C is imperfectly circular is formed inside the multiple-members vibrating portion 31 by the grooves 53A and 53B. That is, without the work of forming a hole in a columnar member, the part of the passage 37 whose cross-section perpendicular to the longitudinal axis C is imperfectly circular is formed inside the multiple-members vibrating portion 31. Forming the groove 53A or 53B corresponding to each of the coupled vibration members 33A and 33B and coupling the coupled vibration members 33A and 33B together are achieved more efficiently than forming a hole in a columnar member without using the gun drill process. Accordingly, manufacturing time and cost of the ultrasonic probe 3 are reduced. The ultrasonic probe 3 is manufactured easily even when the passage 37 has a part whose cross-sectional shape perpendicular to the longitudinal axis C is not perfectly circular.

Next, a function of the ultrasonic treatment device 1 and the ultrasonic probe 3 according to the present embodiment will be described. When living tissue (treatment object) such as a mesentery is treated with the ultrasonic treatment device 1, the ultrasonic vibration is generated with the ultrasonic vibrator 12 by supplying an electric current to the ultrasonic vibrator (ultrasonic transducer) 12 from the ultrasonic-current supply section 7 in accordance with an operation by the input unit 9. Further, the ultrasonic vibration is transmitted to the distal treatment section 30 of the ultrasonic probe 3 along the longitudinal axis C, and the ultrasonic probe 3 longitudinally vibrates accordingly. A high frequency current is supplied from the high-frequency-current supply section 8 in accordance with an operation by the input unit 9. The high frequency current is transmitted to the distal treatment section 30 of the ultrasonic probe 3 and is discharged from the distal treatment section 30. As the distal treatment section 30 is brought into contact with living tissue in this state, the living tissue is thereby burned by the high frequency current, and cutting and coagulation of the living tissue are performed. In the cross-section of the multiple-members vibrating portion 31 perpendicular to the longitudinal axis C where the distal treatment section 30 is located, the first cross-sectional dimension S1 in the first perpendicular directions perpendicular to the longitudinal axis C is greater than the second cross-sectional dimension S2 in the second perpendicular directions perpendicular to both the longitudinal axis C and perpendicular to the first perpendicular directions. For this reason, the distal treatment section 30 is formed in a shape adequate for treatment of the treatment object.

In the ultrasonic probe 3, the single-member vibrating portion 32 is connected at the first anti-node position A1 to the proximal direction side of the multiple-members vibrating portion 31. Accordingly, at the first anti-node position A1 positioned at the proximal end of the multiple-members vibrating portion 31 (distal end of the single-member vibrating portion 32), the number of members which vibrate changes from a state in which only the single integral vibration member 34 vibrates to a state in which a plurality of coupled vibration members 33A and 33B vibrate. At the position where the number of the vibrating members changes, the ultrasonic vibration is easily influenced by stress in directions perpendicular to the longitudinal axis C. When the ultrasonic vibration is influenced by stress, a vibration mode of the ultrasonic vibration changes so as to cause a state in which the ultrasonic probe 3 does not properly perform the longitudinal vibration. As a result, the ultrasonic vibration is not properly transmitted to the distal treatment section 30 of the ultrasonic probe 3.

Accordingly, in the present embodiment, the number of the members which vibrate is configured to change at the first anti-node position A1 through setting. At anti-node positions (loop positions) of the ultrasonic vibration including the first anti-node position A1, a displacement caused by the vibration is maximized while stress in directions perpendicular to the longitudinal axis C is zero. Therefore, the stress does not act on the ultrasonic vibration at the first anti-node position A1 where the number of the vibrating members changes. For this reason, the vibration mode does not change when the number of the vibrating members is changed, and the ultrasonic probe 3 properly performs the longitudinal vibration. In this manner, the ultrasonic vibration is properly transmitted to the distal treatment portion 30 of the ultrasonic probe 3.

When living tissue as a treatment object is burnt by the distal treatment portion 30, a liquid existing surround the tissue or a liquid including the fat produced by a treatment causes a problem in some cases. Therefore, when a treatment object is treated, the suction unit 22 is driven by an operation in the input unit 9. The liquid is suctioned through the opening 39A or opening 39B at the distal treatment portion 30. The liquid (for example, a liquid existing surround tissue or a liquid including the fat produced by a treatment) suctioned from the opening 39A or 38B is suctioned and collected in the suction unit 22 through the passage 37, the space 18, and an inside of the tube member 21.

In the cross-section of the multiple-members vibrating portion 31 perpendicular to the longitudinal axis C, the cross-sectional shape of the passage 37 is formed in an elliptic shape in which the first passage dimension T1 of the passage 37 in the first perpendicular directions is greater than the second passage dimension T2 of the passage 37 in the second perpendicular directions. That is, in the cross-section of the multiple-members vibrating portion 31 perpendicular to the longitudinal axis C, the cross-sectional shape of the passage 37 is formed so as to correspond to the first cross-sectional dimension S1 and second cross-sectional dimension S2 of the cross-section of the multiple-members vibrating portion 31. For this reason, in comparison with the cross-sectional shape of the passage 37 formed in a perfectly circular shape which does not correspond to the first cross-sectional dimension S1 and the second cross-sectional dimension S2 of the cross-sectional shape of the multiple-members vibrating portion 31, the cross-sectional area of the passage 37 perpendicular to the longitudinal axis C in the multiple-members vibrating portion 31 is greater. Since the cross-sectional area of the passage perpendicular to the longitudinal axis C in the multiple-members vibrating portion 31 is greater, the performance of suctioning liquids in treatments improves.

Further, in the cross-section of the multiple-members vibrating portion 31 perpendicular to the longitudinal axis C, the cross-sectional shape of the passage 37 is formed in an analogous shape (analogous form) with respect to the cross-sectional shape of the multiple-members vibrating portion 31. Further, in the cross-section perpendicular to the longitudinal axis C of the multiple-members vibrating portion 31, the first ratio R1 of the first passage dimension T1 of the passage 37 with respect to the first cross-sectional dimension S1 of the multiple-members vibrating portion 31 is equal to the second ratio R2 of the second passage dimension T2 of the passage 37 with respect to the second cross-sectional dimension S2 of the multiple-members vibrating portion 31. Therefore, the cross-sectional area of the passage 37 perpendicular to the longitudinal axis C in the multiple-members vibrating portion 31 is much greater. Accordingly, the performance of suctioning liquids in treatments further improves.

Hence, the ultrasonic probe 3 configured as described above achieves the following advantages. That is, the multiple-members vibrating portion 31 of the ultrasonic probe 3 is manufactured by forming the corresponding groove 53A or 53B in each of the coupled vibration member 33A and 33B and by coupling the coupled vibration members 33A and 33B with respect to each other. A part of the passage 37 whose cross-section perpendicular to the longitudinal axis C has an imperfectly circular shape is formed by the grooves 53A and 53B inside the multiple-members vibrating portion 31. That is, without the work of forming a hole in a columnar member, a part of the passage 37 whose cross-section perpendicular to the longitudinal axis C has an imperfectly circular shape is formed inside the multiple members vibrating portion 31. Forming the corresponding groove 53A or 53B in each of the coupled vibration members 33A and 33B and connecting the coupled vibration members 33A and 33B are achieved more efficiently than forming a hole in a columnar member without using the gun drill process. Accordingly, manufacturing time and cost of the ultrasonic probe 3 are reduced. The ultrasonic probe 3 can be manufactured easily even when the passage 37 has a part whose cross-sectional shape perpendicular to the longitudinal axis C is not perfectly circular.

Further, in the ultrasonic probe 3, a boundary between the single-member vibrating portion 32 and the multiple-members vibrating portion 31 is positioned at the first anti-node position A1. That is, the number of the members which vibrate is configured to change at the first anti-node position A1 by setting. At anti-node positions of the ultrasonic vibration including the first anti-node position A1, the displacement caused by the vibration is maximized while the stress in directions perpendicular to the longitudinal axis C is zero. Therefore, the stress does not act on the ultrasonic vibration at the first anti-node position A1 where the number of the vibrating members changes. For this reason, the vibration mode does not change when the number of the vibrating members is changed, and the ultrasonic probe 3 properly performs the longitudinal vibration. In this manner, even when there is a part where the number of the vibrating members changes, the ultrasonic vibration can be properly transmitted to the distal treatment section 30 of the ultrasonic probe 3.

Modification of First Embodiment

In the first embodiment, the cross-sectional shape of the multiple-members vibrating portion 31 perpendicular to the longitudinal axis C is elliptic, and the cross-sectional shape of the passage 37 in the cross-section of the multiple-members vibrating portion 31 perpendicular to the longitudinal axis C is also elliptic, though not restrictively. For example, as shown in FIG. 7 as the first modification, the cross-sectional shape of the multiple-members vibrating portion 31 perpendicular to the longitudinal axis C may be a rectangle. Also in the present modification, the first cross-sectional dimension S1 in the first perpendicular directions (directions of arrow Y in FIG. 7) perpendicular to the longitudinal axis C is greater than the second cross-sectional dimension S2 in the second perpendicular directions (the directions of arrow Z in FIG. 7) perpendicular to the longitudinal axis C and perpendicular to the first perpendicular directions, in the cross-section of the multiple-members vibrating portions 31 perpendicular to the longitudinal axis C, as in the first embodiment.

Further, in the present modification, in the cross-section of the multiple-members vibrating portion 31 perpendicular to the longitudinal axis C, the cross-sectional shape of the passage 37 is formed in an analogous shape (analogous form) with respect to the cross-sectional shape of the multiple-members vibrating portion 31. Further, in the cross-section of the multiple-members vibrating portion 31 perpendicular to the longitudinal axis C, the first passage dimension T1 of the passage 37 in the first perpendicular directions is greater than the second passage dimension T2 of the passage 37 in the second perpendicular directions. That is, the corresponding groove 53A or 53B is defined to each of the coupled vibration members 33A and 33B in a manner of forming a rectangular cross-sectional shape of the passage in which the first passage dimension T1 of the passage 37 in the first perpendicular directions is greater than the second passage dimension T2 of the passage 37 in the second perpendicular directions, in the cross-section of the multiple-members vibrating portion 31 perpendicular to the longitudinal axis C. The first ratio R1 of the first passage dimension T1 of the passage 37 with respect to the first cross-sectional dimension S1 of the multiple-members vibrating portion 31 is equal to the second ratio R2 of the second passage dimension T2 of the passage 37 with respect to the second cross-sectional dimension S2 of the multiple-members vibrating portion 31.

In the first embodiment, in the cross-section of the multiple-members vibrating portion 31 perpendicular to the longitudinal axis C, the cross-sectional shape of the passage 37 is formed, though not restrictively, in an analogous shape with respect to the cross-sectional shape of the multiple-members vibrating portion 31. For example, as shown in FIG. 8 as the second modification, the cross-sectional shape of the multiple-members vibrating portion 31 perpendicular to the longitudinal axis C may be rectangle, while the cross-sectional shape of the passage 37 in the cross-section of the multiple-members vibrating portion 31 perpendicular to the longitudinal axis C may be elliptic. Also in the present modification, the first cross-sectional dimension S1 in the first perpendicular directions (directions of arrow Y in FIG. 8) perpendicular to the longitudinal axis C is greater than the second cross-sectional dimension S2 in the second perpendicular directions (the directions of arrow Z in FIG. 8) perpendicular to the longitudinal axis C and perpendicular to the first perpendicular directions, in the cross-section of the multiple-members vibrating portion 31 perpendicular to the longitudinal axis C, as in the first embodiment. Further, in the cross-section of the multiple-members vibrating portion 31 perpendicular to the longitudinal axis C, the first passage dimension T1 of the passage 37 in the first perpendicular directions is greater than the second passage dimension T2 of the passage 37 in the second perpendicular directions.

From the first and second modifications, in the cross-section of the multiple-members vibrating portion 31 perpendicular to the longitudinal axis C, the cross-sectional shape of the passage 37 may be formed so as to correspond to the first cross-sectional dimension S1 and second cross-sectional dimension S2 of the cross-section of the multiple-members vibrating portion 31. In this manner, in comparison with the cross-sectional shape of the passage 37 formed in a perfectly circular shape which does not correspond to the first cross-sectional dimension S1 and the second cross-sectional dimension S2 of the cross-sectional shape of the multiple-members vibrating portion 31, the cross-sectional area of the passage 37 perpendicular to the longitudinal axis C in the multiple-members vibrating portion 31 is greater. Since the cross-sectional area of the passage perpendicular to the longitudinal axis C in the multiple-members vibrating portion 31 is greater, the performance of suctioning liquids in treatments improves.

Second Embodiment

Next, the second embodiment of the present invention will be described with reference to FIGS. 9, 10A, and 10B. The second embodiment is achieved by modifying the first embodiment as follows. The same components as those of the first embodiment will be denoted respectively by the same reference symbols, and detailed descriptions thereof will be omitted herefrom.

Figure 9:
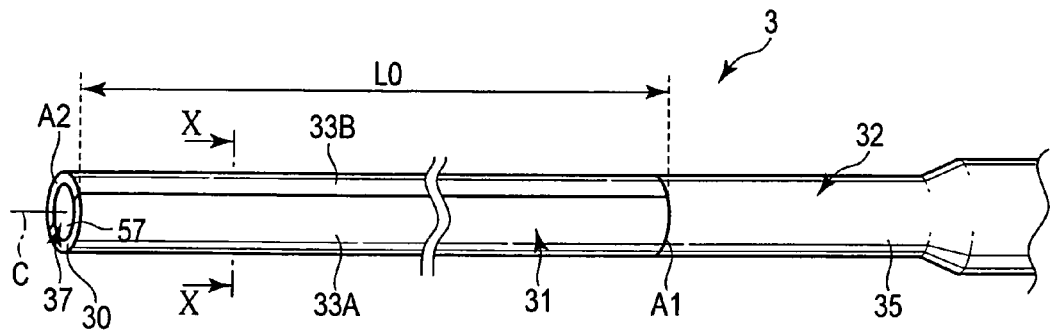
FIG. 9 is a perspective view schematically showing an ultrasonic probe according to a second embodiment of the invention.

FIG. 9 shows an ultrasonic probe 3 according to the present embodiment. FIG. 10A shows an example of a cross-section cut along line X-X in FIG. 9, and FIG. 10B shows another example of the cross-section cut along line X-X in FIG. 9. As shown in FIG. 9, also in the present embodiment, the coupled vibration members 33A and 33B in a multiple-members vibrating portion 31 extend along a longitudinal axis C between a first anti-node (loop) position A1 and a second anti-node position A2, as in the first embodiment. At the first anti-node position A1, an ultrasonic vibration is transmitted to the multiple-members vibrating portion 31 from a single-member vibrating portion 32. That is, the single-member vibrating portion 32 is connected to a proximal direction side of the multiple-members vibrating portion 31 at the first anti-node position A1. Further, a distal end of the ultrasonic probe 3 exists at the second anti-node position A2. The multiple-members vibrating portion 31 of the ultrasonic probe 3 has a reference size L0 along the longitudinal axis C from the first anti-node position A1 to the second anti-node position A2.

Figure 10A:
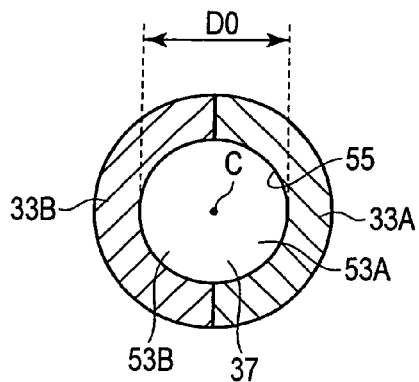
FIG. 10A is a cross-sectional view showing an example of a cross-section cut along line X-X in FIG. 9.
Figure 10B:
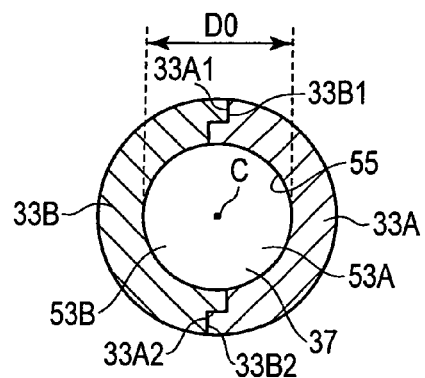
FIG. 10B is a cross-sectional view showing another example of a cross-section cut along line X-X in FIG. 9.

As shown in FIG. 10A and FIG. 10B, in the present embodiment differing from the first embodiment, a cross-sectional shape of the multiple-members vibrating portion 31 perpendicular to the longitudinal axis C is formed in a perfectly circular shape. Further, in a cross-section of the multiple-members vibrating portion 31 perpendicular to the longitudinal axis C, the cross-sectional shape of a passage 37 is also formed in a perfectly circular shape. The cross-sectional shape of the passage 37 in the multiple-members vibrating portion 31 has a diameter D0 greater than or equal to $\frac{1}{100}$ of the reference size L0 along the longitudinal axis C from the first anti-node position A1 to the second anti-node position A2. That is, a corresponding groove 53A or 53B is defined to each of the coupled vibration members 33A and 33B in a manner of forming a perfectly circular cross-sectional shape of the passage which has the diameter D0 greater than or equal to $\frac{1}{100}$ of the reference size L0 along the longitudinal axis C from the first anti-node position A1 to the second anti-node position A2, in the cross-section of the multiple-members vibrating portion 31 perpendicular to the longitudinal axis C.

In the first embodiment, the coupled vibration members 33A and 33B are connected, though not restrictively, by engagement protrusions 43A and 43B and engagement grooves 45A and 45B. For example, as shown in FIG. 10B, in place of the engagement protrusions 43A and 43B and engagement grooves 45A and 45B, step portions 33A1 and 33A2 may be provided to the coupled vibration member 33A, and step portions 33B1 and 33B2 may be provided to the coupled vibration member 33B. Further, by engaging the step portions 33A1 and 33B1 with respect to each other as well as the step portions 33A2 and 33B2 with respect to each other, the coupled vibration members 33A and 33B are positioned and connected with respect to each other.

In the present embodiment differing from the first embodiment, openings 39A and 39B are not provided but an opening 57 which is open toward the distal direction is provided to a distal end portion (distal treatment section 30) of the ultrasonic probe 3. As the coupled vibration members 33A and 33B are coupled with respect to each other, the opening 57 is formed by distal ends of the grooves 53A and 53B.

In the present embodiment, the distal treatment section 30 does not need to be used as an electric knife, and a treatment of a treatment object as described in the first embodiment does not need to be performed by the distal treatment section 30. That is, a power supply unit 6 does not need to be provided with a high-frequency-current supply section 8, and a high frequency current does not need to be transmitted to the distal treatment section 30. In this case, for example, the ultrasonic treatment device 1 includes a liquid feed (supply) unit (not shown). An ultrasonic vibration is transmitted to the distal treatment section 30, and a liquid such as physiological saline is fed to the vicinity of a treatment object through a liquid feed (supply) passage (not shown) such as a liquid feed tube. Accordingly, cavitation occurs near the distal treatment section 30 and causes a treatment object such as hepatic cells to be shattered and emulsified, thereby performing a resection of the treatment object. The treatment object resected is suctioned from the opening 57. Further through the passage 37, a space 18, and an inside of a tube member 21, the resected treatment object is suctioned and collected in the suction unit 22.

In the present embodiment, as in the first embodiment, the number of members which vibrate is configured to change at the first anti-node position A1 by setting. As described previously, at anti-node positions of the ultrasonic vibration including the first anti-node position A1, a displacement caused by the vibration is maximized while the stress in directions perpendicular to the longitudinal axis C is zero. Therefore, the stress does not affect the ultrasonic vibration at the first anti-node position A1 where the number of the vibrating members changes. For this reason, the vibration mode does not change when the number of the vibrating members is changed, and the ultrasonic probe 3 properly performs the longitudinal vibration. In this manner, the ultrasonic vibration is properly transmitted to the distal treatment section 30 of the ultrasonic probe 3.

The ultrasonic probe 3 according to the present embodiment is manufactured in the same manner as the ultrasonic probe according to the first embodiment. The ultrasonic probe 3 has a small outer diameter and a large dimension along the longitudinal axis C. It is therefore difficult to form a hole in the elongated (long and narrow) ultrasonic probe 3 through a gun drill process. For example, when a hole which has a diameter D0 greater than or equal to $1/100$ of a reference dimension L0 along the longitudinal axis C from the first anti-node position A1 to the second anti-node position A2 is formed as a part of the passage 37 in the multiple-members vibrating portion 31, the ultrasonic probe 3 is then thinned and therefore makes use of the gun drill process difficult. Inability to use the gun drill process causes deterioration in work efficiency of forming a hole to form a part of the passage 37 in the columnar member.

Hence, in the present embodiment, a corresponding groove 53A or 53B is formed in each of the coupled vibration members 33A and 33B, so as to connect the coupled vibration members 33A and 33B with respect to each other. A part of the passage 37 whose diameter D is greater than or equal to $1/100$ of the reference dimension L0 is formed inside the multiple-members vibrating portion 31 by the grooves 53A and 53B. That is, without the work of forming a hole in a columnar member, the part of the passage 37 whose diameter D is greater than or equal to $1/100$ of the reference dimension L0 along the longitudinal axis C from the first anti-node position A1 to the second anti-node position A2 is formed inside the multiple-members vibrating portion 31. Forming the corresponding groove 53A or 53B in each of the coupled vibration members 33A and 33B and coupling the coupled vibration members 33A and 33B are achieved more efficiently than forming a hole in a columnar member without using the gun drill process. Accordingly, the ultrasonic probe 3 is easily manufactured even when a hole which has the diameter D0 greater than or equal to $1/100$ of the reference dimension L0 along the longitudinal axis C from the first anti-node position A1 to the second anti-node position A2 is formed as a part of the passage 37 in the multiple-members vibrating portion 31.

Hence, the ultrasonic probe 3 configured as described above provides the following advantages. That is, the multiple-members vibrating portion 31 of the ultrasonic probe 3 is manufactured by forming the corresponding groove 53A or 53B in each of the coupled vibration members 33A and 33B and by coupling the coupled vibration members 33A and 33B with respect to each other. Further, inside the multiple-members vibrating portion 31, a part of the passage 37 whose diameter D is greater than or equal to $1/100$ of the reference dimension L0 along the longitudinal axis C from the first anti-node position A1 to the second anti-node position A2 is formed by the grooves 53A and 53B. That is, without the work of forming a hole in a columnar member, the part of the passage 37 whose diameter D is greater than or equal to $1/100$ of the reference dimension L0 along the longitudinal axis C from the first anti-node position A1 to the second anti-node position A2 is formed inside the multiple-members vibrating portion 31. Forming the grooves 53A or 53B corresponding to each of the coupled vibration members 33A and 33B and coupling the coupled vibration members 33A and 33B are achieved more efficiently than forming a hole in a columnar member without using the gun drill process. Therefore, manufacturing time and cost for the ultrasonic probe 3 are reduced, and the ultrasonic probe 3 is easily manufactured even when a hole whose diameter D is greater than or equal to $1/100$ of the reference dimension L0 along the longitudinal axis C from the first anti-node position A1 to the second anti-node position A2 is formed as a part of the passage 37.

Further, in the ultrasonic probe 3, a boundary between the single-member vibrating portion 32 and the multiple-members vibrating portion 31 is located at the first anti-node (loop) position A1. That is, the number of the members which vibrate is configured to change at the first anti-node position A1 by setting. At anti-node positions of the ultrasonic vibration including the first anti-node position A1, the displacement caused by the vibration is maximized while the stress in directions perpendicular to the longitudinal axis C is zero. Therefore, the stress does not affect the ultrasonic vibration at the first anti-node position A1 where the number of the vibrating members changes. For this reason, the vibration mode does not change when the number of the vibrating members is changed, and the ultrasonic probe 3 properly performs the longitudinal vibration. In this manner, even when there is a part where the number of the vibrating members changes, the ultrasonic vibration can be properly transmitted to the distal treatment section 30 of the ultrasonic probe 3.

Other Modifications

As shown in FIG. 11 as the third modification, the cross-sectional shape perpendicular to the longitudinal axis C of the multiple-members vibrating portion 31 may be a square. In the present modification, the corresponding groove 53A or 53B is defined in each of the coupled vibration members 33A and 33B in a manner of forming a square cross-sectional shape of the passage in the cross-section of the multiple-members vibrating portion 31 perpendicular to the longitudinal axis C.

As has been described in the first embodiment, a hole in which the cross-sectional shape of the passage is not perfectly circular in the cross-section perpendicular to the longitudinal axis C cannot be formed in a columnar member through the gun drill process. Hence, in the present modification, the corresponding groove 53A or 53B is formed in each of the coupled vibration members 33A and 33B, so as to connect the coupled vibration members 33A and 33B with respect to each other. Further, a part of the passage 37 whose cross-section perpendicular to the longitudinal axis C is not a perfectly circular shape is formed inside the multiple-members vibrating portion 31 by the grooves 53A and 53B. Forming the groove 53A or 53B corresponding to each of the coupled vibration members 33A and 33B and coupling the coupled vibration members 33A and 33B with respect to each other are achieved more efficiently than forming a hole in a columnar member without using the gun drill process.

As shown in FIG. 12 as the fourth modification, a meandering passage portion 61 in which the passage 37 meanders with respect to the longitudinal axis C may be formed inside the multiple-members vibrating portion 31. In the present modification, the corresponding groove 53A or 53B is defined to each of the coupled vibration members 33A and 33B in a manner of forming the meandering passage portion 61 inside the multiple-members vibrating portion 31. Since the winding passage potion 61 is provided, the whole length of the passage 37 is longer than the passage 37 formed along the longitudinal axis C. As the whole length of the passage 37 is longer, the volume occupied by the passage 37 increases to be greater. When an ultrasonic vibration and a high frequency current are transmitted to the ultrasonic probe 3, the ultrasonic probe 3 generates heat due to the ultrasonic vibration and the high frequency current. In the present modification, the volume occupied by the passage 37 is greater, and the heat capacity of the ultrasonic probe 3 decreases so as to improve the heat exchange property of the ultrasonic probe 3. Therefore, when the ultrasonic probe 3 generates heat due to the ultrasonic vibration and high frequency current, the ultrasonic probe 3 is cooled effectively.

However, a hole including the meandering passage portion 61 which meanders with respect to the longitudinal axis C cannot be formed in a columnar member through the gun drill process. Hence, in the present modification, the corresponding groove 53A or 53B is formed in each of the coupled vibration members 33A and 33B, so as to connect the coupled vibration members 33A and 33B with respect to each other. Further, a part of the passage 37 including the meandering passage portion 61 which meanders with respect to the longitudinal axis C is formed inside the multiple-members vibrating portion 31 by the grooves 53A and 53B. Forming the groove 53A or 53B corresponding to each of the coupled vibration members 33A and 33B and coupling the coupled vibration members 33A and 33B with respect to each other are achieved more efficiently than forming a hole in a columnar member without using the gun drill process.

As shown in FIG. 13 as the fifth modification, a cross-sectional-area changed portion 62 whose cross-sectional area of the passage 37 perpendicular to the longitudinal axis C changes may be formed inside the multiple-members vibrating portion 31. In the present modification, the groove 53A or 53B is defined in relation to each of the coupled vibration members 33A and 33B in a manner of forming the cross-sectional-area changed portion 62 inside the multiple-members vibrating portion 31. The cross-sectional-area changed portion 62 extends from the opening 57 toward the proximal direction. In the cross-sectional-area changed portion 62, the sectional area of the passage increases as going toward the proximal direction. By providing the cross-sectional-area changed portion 62 in which the cross-sectional area of the passage increases as it goes toward the proximal direction, a suction pressure at the opening 57 is greater than when the cross-sectional-area changed portion 62 is not provided. Further, the cross-sectional area of the passage is most-minimized at the opening 57 in the passage 37 since the passage-sectional-area changed portion 62 is provided. Therefore, it is hard for fat and living tissue suctioned through the opening 57 to remain in the middle of the passage 37.

However, a hole including the cross-sectional-area changed portion 62 whose cross-sectional area perpendicular to the longitudinal axis C is changed cannot be formed in a columnar member by the gun drill process. Hence, in the present modification, the groove 53A is formed in the coupled vibration member 33A and the groove 53B is formed in the coupled vibration member 33B, so as to connect the coupled vibration members 33A and 33B with respect to each other. Further, a part of the passage 37 including the cross-sectional-area changed portion 62 whose cross-sectional area perpendicular to the longitudinal axis C is changed is formed inside the multiple-members vibrating portion 31 by the grooves 53A and 53B. Forming the groove 53A or 53B corresponding to each of the coupled vibration members 33A and 33B and coupling the coupled vibration members 33A and 33B with respect to each other are achieved more efficiently than forming a hole in a columnar member without using the gun drill process.

Also in the embodiment described above, the ultrasonic probe 3 is provided with the single-member vibrating portion 32, though not restrictively. For example, as shown in FIG. 14 as the sixth modification, the multiple-members vibrating portion 31 may be directly connected to the vibration generation unit 2. In the present modification, the single-member vibrating portion 32 is not formed in the ultrasonic probe 3. As a male screw portion 48 is screwed in a female screw portion 19 of a horn 15, the vibration generation unit 2 is connected to the proximal direction side of the multiple-members vibrating portion 31 at the first anti-node position A1. That is, the male screw portion 48 serves as a joint portion capable of connecting the vibration generation unit 2 directly to the proximal direction side of the multiple-members vibrating portion 31 at the first anti-node position A1. In the present modification, the whole passage 37 is formed inside the multiple-members vibrating portion 31 by the grooves 53A and 53B.

Further, in the present modification, it is changed at the first anti-node position A1 from a state in which a single horn 15 vibrates into a state in which a plurality of coupled vibration members 33A and 33B vibrate. That is, the number of members which vibrate is configured to change at the first anti-node position A1 by setting. At anti-node positions of the ultrasonic vibration including the first anti-node position A1, the displacement caused by the vibration is maximized while the stress in directions perpendicular to the longitudinal axis C is zero. Therefore, the stress does not affect the ultrasonic vibration at the first anti-node position A1 where the number of the vibrating members changes. For this reason, the vibration mode does not change when the number of the vibrating members is changed, and the ultrasonic probe 3 properly performs the longitudinal vibration. In this manner, the ultrasonic vibration is properly transmitted to the distal treatment section 30 of the ultrasonic probe 3.

In the embodiments described above, the second anti-node position A2 corresponds, though not restrictively, to the distal end of the ultrasonic probe 3. For example, as shown in FIG. 15 as the seventh modification, another single-member vibrating portion 63 different from the single-member vibrating portion 32 may be provided to the distal direction side of the multiple-members vibrating portion 31. The single-member vibrating portion 63 is formed by an integral vibration member 65 alone. When the ultrasonic vibration is transmitted, the integral vibration member 65 vibrates in the same mode as the coupled vibration members 33A and 33B. The single-member vibrating portion 63 is connected directly to the distal direction side of the multiple-members vibrating portion 31 at the second anti-node position A2. Further, the distal end of the single-member vibrating portion 63 is also the distal end of the ultrasonic probe 3, and corresponds to a third anti-node (loop) position A3 of the ultrasonic vibration located to the distal direction side of the second anti-node position A2.

Further, in the present modification, it is changed at the second anti-node position A2 from a state in which the plurality of coupled vibration members 33A and 33B vibrate into a state in which a single integral vibration member 65 vibrates. That is, the number of members which vibrate is configured to change at the second anti-node position by setting. At anti-node positions of the ultrasonic vibration including the second anti-node position A2, the displacement caused by the vibration is maximized while the stress in directions perpendicular to the longitudinal axis C is zero. Therefore, the stress does not affect the ultrasonic vibration at the second anti-node position A2 where the number of the vibrating members changes. For this reason, the vibration mode does not change when the number of the vibrating members is changed, and the ultrasonic probe 3 properly performs the longitudinal vibration. In this manner, the ultrasonic vibration is properly transmitted to the distal treatment section 30 of the ultrasonic probe 3.

Also in the embodiment described above, the ultrasonic probe 3 is provided with, though not restrictively, two coupled vibration members 33A and 33B. For example, as shown in FIG. 16 as the eighth modification, the multiple-members vibrating portion 31 may include three coupled vibration members 33A, 33B, and 33C. Also in the present modification, the coupled vibration members 33A, 33B, and 33C are connected with respect to each other, and each of the coupled vibration members 33A, 33B, and 33C extends along the longitudinal axis C between the first anti-node position A1 and the second anti-node position A2. When the ultrasonic vibration is transmitted, the coupled vibration member 33A vibrates in the same vibration mode as the other coupled vibration members 33B and 33C.

In the present modification, a corresponding groove 53A, 53B, or 53C is defined in each of the coupled vibration members 33A, 33B, and 33C by a groove defining portion 55. The groove 53A of the coupled vibration member 33A cooperates with the grooves 53B and 53C of the other coupled vibration members 33B and 33C, thereby forming a part of the passage 37 inside the multiple-members vibrating portion 31.

Also in the embodiments described above, the passage 37 of the ultrasonic probe 3 is provided, though not restrictively, as a suction passage where a liquid to be suctioned flows. For example, liquids may be supplied to the vicinity of a treatment object through the passage 37.

From the modification described above, the ultrasonic probe 3 needs only to includes the multiple-members vibrating portion 31 including the plurality of coupled vibration members (33A, 33B, and 33C) which are connected with respect to each other and each of which extends along the longitudinal axis C between the first anti-node position A1 and the second anti-node position A2. Further, when the ultrasonic vibration is transmitted, each one (for example, 33A) of the coupled vibration members may vibrate in the same vibration mode as the other coupled vibration members (for example, 33B and 33C). Still further, the groove (for example, 53A) of each one (for example, 33A) of the coupled vibration members may cooperate with the other grooves (for example, 53A and 53B) of the other coupled vibration members (33B and 33C), thereby forming a part of the passage 37 inside the multiple-members vibrating portion 31.

With the configuration as described above, the ultrasonic probe 3 can be easily manufactured irrespective of the type of the passage 37 provided inside. Further, even when a part where the number of the vibrating members changes exists, the ultrasonic vibration can be properly transmitted to the distal treatment section 30 of the ultrasonic probe 3.

Hereinafter, other characterizing technical features of the invention will be described below for reference:

(Additional Note 1)

An ultrasonic probe which is configured to transmit an ultrasonic vibration from a proximal direction toward a distal direction along a longitudinal axis, the probe comprising:
a passage defining portion which defines a passage inside the ultrasonic probe from a distal end portion of the ultrasonic probe toward the proximal direction;
a multiple-members vibrating portion including a plurality of coupled vibration members which are connected with respect to each other and each of which extends along the longitudinal axis between a first anti-node position of the ultrasonic vibration and a second anti-node position of the ultrasonic vibration located to a distal direction side of the first anti-node position, each of the coupled vibration members being configured to vibrate in the same vibration mode as other coupled vibration member when the ultrasonic vibration is transmitted; and
a groove defining portion which is provide to the passage defining portion, and which defines a groove in each of the coupled vibration members, each of the groove being configured to cooperate with a groove of the other coupled vibration member, and thereby being configured to form at least a part of the passage inside the multiple-members vibrating portion.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment probe that is configured to transmit an ultrasonic vibration from a proximal direction toward a distal direction along a longitudinal axis, the ultrasonic treatment probe comprising:
a multiple-members vibrating portion that includes a plurality of coupled vibration members, each of the coupled vibration members extending in a lengthwise direction along the longitudinal axis, and each of the coupled vibration members having an inner surface, wherein
a groove is formed in the lengthwise direction along the longitudinal axis by the inner surface in each of the coupled vibration members, the coupled vibration members being coupled to each other when the inner surface of each of the coupled vibration members face each other, such that a passage extending from the proximal direction toward the distal direction is formed inside the multiple-members vibrating portion; and
the multiple-members vibrating portion is configured to transmit the ultrasonic vibration such that each of the coupled vibration members vibrates in a same vibration mode, and such that a first anti-node position of the ultrasonic vibration is located at a proximal end of the multiple-members vibrating portion, and a second anti-node position of the ultrasonic vibration is located at a distal end of the multiple members vibrating portion.

2. The ultrasonic treatment probe according to claim 1, further comprising:
a single-member vibrating portion which is formed by a single integral vibration member alone, the integral vibration member being configured to vibrate in the same vibration mode as the coupled vibration members when the ultrasonic vibration is transmitted, and the single-member vibrating portion being connected to a proximal direction side of the multiple-members vibrating portion at the first anti-node position of the ultrasonic vibration.

3. The ultrasonic treatment probe according to claim 1, further comprising
a joint portion configured to connect a vibration generation unit, which is configured to generate the ultrasonic vibration, directly to a proximal direction side of the multiple-members vibrating portion at the first anti-node position of the ultrasonic vibration.

4. The ultrasonic treatment probe according to claim 1, wherein
the multiple-members vibrating portion has a cross-sectional shape, and the passage has a cross-sectional shape;

when a direction perpendicular to the longitudinal axis is defined as a first perpendicular direction, and a direction perpendicular to both the longitudinal axis and the first perpendicular direction is defined as a second perpendicular direction, a first cross-sectional dimension of the multiple-members vibrating portion in the first perpendicular direction is greater than a second cross-sectional dimension of the multiple-members vibrating portion in the second perpendicular direction;

a first passage dimension of the passage in the first perpendicular direction is greater than a second passage dimension of the passage in the second perpendicular direction.

5. The ultrasonic treatment probe according to claim 4, wherein the cross-sectional shape of the passage is a same shape as the cross-sectional shape of the multiple-members vibrating portion; and a first ratio of the first passage dimension of the passage with respect to the first cross-sectional dimension of the multiple-members vibrating portion is equal to a second ratio of the second passage dimension of the passage with respect to the second cross-sectional dimension of the multiple-members vibrating portion.

6. The ultrasonic treatment probe according to claim 1, wherein the distal end of the multiple-members vibrating portion forms a distal end of the ultrasonic treatment probe.

* * * * *